(12) United States Patent
Boon-Falleur et al.

(10) Patent No.: US 6,379,901 B1
(45) Date of Patent: Apr. 30, 2002

(54) METHOD FOR SCREENING FOR CANCER USING BINDERS FOR MAGE RELATED PEPTIDES AND COMPLEXES OF THE PEPTIDE AND HLA MOLECULES

(75) Inventors: Thierry Boon-Falleur; Pierre van der Bruggen; Etienne De Plaen; Christophe Lurguin, all of Brussels (BE); Catia Traversari, Milan (IT); Beatrice Gaugler; Benoit Van den Eynde, both of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 08/443,580

(22) Filed: May 17, 1995

(51) Int. Cl.$^7$ .................. G01N 33/53; G01N 33/567; G01N 33/574
(52) U.S. Cl. .................. 435/7.1; 435/7.21; 435/7.23; 530/328
(58) Field of Search ................ 435/7.1, 47.21, 435/7.23; 530/328

(56) References Cited

U.S. PATENT DOCUMENTS

| | | | |
|---|---|---|---|
| 4,492,760 A | * | 1/1985 | DeFreitas et al. |
| 4,707,438 A | * | 11/1987 | Icegdar et al. |
| 5,342,774 A | | 8/1994 | Boon et al. |
| 5,405,940 A | | 4/1995 | Boon et al. |

FOREIGN PATENT DOCUMENTS

| | | | |
|---|---|---|---|
| WO | 89/07146 | * | 8/1989 |
| WO | WO9202543 | | 2/1992 |
| WO | WO9220356 | | 11/1992 |
| WO | WO940320 | | 2/1994 |

OTHER PUBLICATIONS

Rötzschke et al., "Isolated and analysis of naturally processed Viral peptides as recognized by cytolytic T cells", Nature 348: 252–254 (1990).

Van der Bruggen et al., "A Gene Encoding An Antigen Recognized By Cytolytic T Lymphocytes on a Human Malanoma", Science 254: 1643–1647 (Dec. 1991).

Traversari et al., "A Nonapeptide Encoded by Human Gene MAGE–1 Is Recognized on HLA–A1 by Cytolytic T Lymphocytes Directed Against Tumor Antigen MZ2–E". J.Exp.Med. 176: 1453–1457 (1992).

* cited by examiner

Primary Examiner—Christina Y. Chan
Assistant Examiner—Marianne Debrino
(74) Attorney, Agent, or Firm—Fulbright & Jaworski, LLP

(57) ABSTRACT

The invention involves a nonapeptide derived from the tumor rejection antigen precursor encoded by gene MAGE-3. This nonapeptide is presented by the HLA molecule HLA-A1. The resulting complexes are identified by cytolytic T cells. Such recognition may be used in diagnostics, or therapeutically.

2 Claims, 8 Drawing Sheets

FIG. 4

```
MAGE 1     E    A    D    P    T    G    H    S    Y
MAGE 2     E    V    V    P    I    S    H    L    Y
MAGE 21    E    V    V    R    I    G    H    L    Y
MAGE 3     E    V    D    P    I    G    H    L    Y
MAGE 4     E    V    D    P    A    S    N    T    Y
MAGE 41    E    V    D    P    T    S    N    T    Y
MAGE 5     E    A    D    P    T    S    N    T    Y
MAGE 51    E    A    D    P    T    S    N    T    Y
MAGE 6     E    V    D    P    I    G    H    V    Y

MAGE 1     GAA  GCA  GAC  CCC  ACC  GGC  CAC  TCC  TAT
MAGE 2     GAA  GTG  GTC  CCC  ATC  AGC  CAC  TTG  TAC
MAGE 21    GAA  GTG  GTC  CGC  ATC  GGC  CAC  TTG  TAC
MAGE 3     GAA  GTG  GAC  CCC  ATC  GGC  CAC  TTG  TAC
MAGE 4     GAA  GTG  GAC  CCC  GCC  AGC  AAC  ACC  TAC
MAGE 41    GAA  GTG  GAC  CCC  ACC  AGC  AAC  ACC  TAC
MAGE 5     GAA  GCG  GAC  CCC  ACC  AGC  AAC  ACC  TAC
MAGE 51    GAA  GCG  GAC  CCC  ACC  AGC  AAC  ACC  TAC
MAGE 6     GAA  GTG  GAC  CCC  ATC  GGC  CAC  GTG  TAC
```

US 6,379,901 B1

METHOD FOR SCREENING FOR CANCER USING BINDERS FOR MAGE RELATED PEPTIDES AND COMPLEXES OF THE PEPTIDE AND HLA MOLECULES

FIELD OF THE INVENTION

This invention relates to immunogenetics and to peptide chemistry. More particularly, it relates to a nonapeptide useful in various ways, including as an immunogen and as a target for the HLA-A1 molecule. More particularly, it relates to a so-called "tumor rejection antigen", derived from the tumor rejection antigen precursor encoded by gene MAGE-3, and presented by human leukocyte antigens of HLA-A1.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum antigens are obtained by mutating tumor cells which do not generate an immune response in syngeneic mice and will form tumors (i.e., "tum$^+$" cells). When these tum$^+$cells are mutagenized, they are rejected by syngeneic mice, and fail to form tumors (thus "tum$^{31}$"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum variants fail to form progressive tumors because they initiate an immune rejection process. The evidence in favor of this hypothesis includes the ability of "tum$^{31}$" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum$^{31}$ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum$^{31}$ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearson et al., Cancer Res. 48: 2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLS, including minor histocompatibility antigens, the male specific H-Y antigens, and the class of antigens referred to as "tum$^{31}$" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum$^{31}$ variants following mutagenesis, including variants referred to as P91A (DePlaen, supra), 35B (Szikora, supra), and P198 (Sibille, supra). In contrast to tumor rejection antigens —and this is a key distinction —the tum$^{31}$ antigens are only present after the tumor cells are mutagenized. Tumor rejection antigens are present on cells of a given tumor without mutagenesis. Hence, with reference to the literature, a cell line can be tum$^+$, such as the line referred to as "P1", and can be provoked to produce tum$^{31}$ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A', 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that a particular nonapeptide is in fact presented on the surface of tumor cells, and that the presentation of the nonapeptide requires that the presenting molecule be HLA-A1. Complexes of the MAGE-1 tumor rejection antigen (the "TRA" or "nonapeptide") leads to lysis of the cell presenting it by cytolytic T cells ("CTLs"). This observation has both diagnostic and therapeutic implications, as discussed herein.

Research presented in, e.g., U.S. patent application Ser. No. 07/938,334 filed Aug.31, 1992, now U.S. Pat. No. 5,405,940, which is the parent of the subject application showed that, when comparing homologous regions of various MAGE genes to the region of the MAGE-1 gene coding for the relevant nonapeptide, there is a great deal of homology. Indeed, these observations lead to one of the aspects of the invention disclosed and claimed therein, which is a family of nonapeptides all of which have the same N-terminal and C-terminal amino acids. These nonapeptides were described as being useful for various purposes which includes their use as immunogens, either alone or coupled to carrier peptides. Nonapeptides are of sufficient size to constitute an antigenic epitope, and the antibodies generated thereto were described as being useful for identifying the nonapeptide, either as it exists alone, or as part of a larger polypeptide.

The nonapeptides were described as being useful for identifying various HLA subtypes on the surface of tumor cells, such as melanomas. Via this ability they served both as diagnostic markers and as therapeutic agents. These features are discussed infra.

The nucleic acid sequences which code for the nonapeptides were also described therein. These nucleic acid sequences were described as also being useful as diagnostic probes for tumor presence.

The application also showed how it had been found that a cellular model could be used, wherein a non-human cell can be transfected with a nucleic acid sequence coding for a human HLA molecule. The resulting transfectant could then be used to test for nonapeptide specificity of the particular HLA molecule, or as the object of a second transfection with a MAGE gene. The co-transfectant could be used to determine whether the particular MAGE based TRA is presented by the particular HLA molecule.

The present invention deals with one of the peptides described in the earlier of the two parent application. Specifically, the nonapeptide Glu Val Asp Pro Ile Gly His Leu Tyr (Seq. I.D. No: 17) derived from the tumor rejection antigen precursor coded for by MAGE-3 has now been found to be presented by human leukocyte antigen HLA-A1. This finding and the ramifications thereof are described in the disclosure which follows.

BRIEF DESCRIPTION OF THE FIGURES

FIG. 3 (A and B) compares lysis of mouse cells transfected with HLA-A1 genes, in the presence of the MAGE-1 nonapeptide, and when cotransfected with the sequence coding for MAGE-1.

FIG. 4 compares nonapeptides from various homologous sections of MAGE genes and the nucleic acid sequences coding for these nonapeptide.

Figure 1:
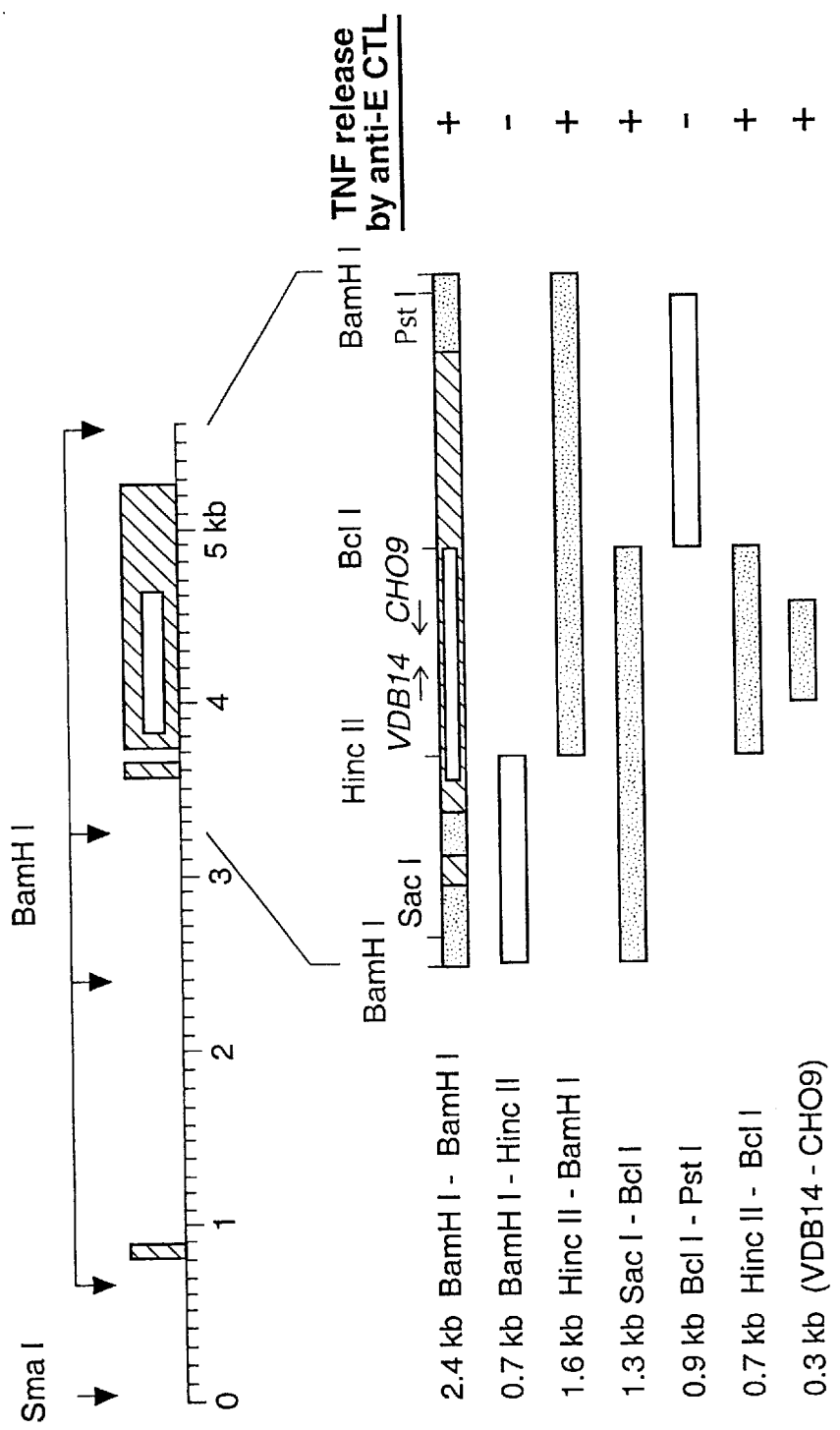
FIG. 1 outlines the procedure by which a 300 base pair fragment of MAGE-1 gene was identified as coding for the relevant tumor rejection antigen.

SEQ ID NOS: 1–9 show nucleic acid molecules which encode homologous MAGE peptides.

DETAILED DESCRIPTION OF PREFERRED EMBODIMENTS

EXAMPLE 1

The 2.4 Kb BamIII fragment, described by van der Bruggen et al., Science 254: 1643 (1991), the disclosure of which is incorporated by reference, is known to contain only exons 2 and 3 of the gene coding for MAGE-1 protein. The fragment transfers expression of antigen MZ2-E to E⁻ antigen loss cell line variant MZ2-MEL.2.2, and leads to lysis of the transfectants by E⁺CTLs. Previous work by DePlaen et al., Proc. Natl. Acad. Sci. USA 85: 2274 (1988), and Chomez et al., Immunogenetics 35: 241 (1990), had established that small gene fragments containing antigen peptide coding sequences regularly express those antigens, even when not transfected in the form of expression vectors. In view of these observations, experiments were carried out with smaller fragments of the 2.4 kb fragment. Various restriction enzymes were used to cut the 2.4 kb fragment into smaller fragments. The resulting, smaller fragments were cloned into plasmid vector pTZ18R. A 300 base pair fragment taken from exon 3 was obtained via polymerase chain reaction ("PCR") amplification, using oligonucleotides VDB 14(SEQ ID NO: 10):

5'-CAGGGAGCCAGTCACAAAG-3'
and CHO 9(SEQ ID NO: 11):
5'-ACTCAGCTCCTCCCAGATTT-3'.

These primers amplify a 300 base pair fragment of MAGE 1, between positions 422 and 722 of exon 1. The fragment was cloned into expression vector PSVK3. The new constructs were cotransfected with plasmid pSVtkneoβ into the MZ2. MEL 2.2 cell lines. This was accomplished using the calcium phosphate precipitation method (Traversari et al., Immunogenetics 35: 145 (1992); Wölfel et al., Immunogenetics 26: 178 (1987)), using $4 \times 10^6$ cells and 3 ug of pSVtneoβ (Nicolas et al., CSH Conf. Cell Prolif 10: 469 (1983)), and 30 ug of the pTZ18R or PSVK3 constructs. The transfectants were then selected in medium containing neomycin analog G418. Fifteen days after transfection, resistant cells were tested for their ability to stimulate TNF production by the anti-E antigen specific CTL 82/30. This was accomplished by adding 100 ul samples, containing 1500 cells of CTL 82/30 to $4 \times 10^4$ transfected cells. Supernatant samples (50 ul) were harvested and added to $3 \times 10^4$ WEHI 164 clone 13 cells (Espevik et al., J. Immunol. Meth. 95: 99 (1986)), to evaluate TNF presence. Mortality of WEHI cells was estimated 24 hours later, using an MTT colorimatric assay as per, e.g., Traversari et al., supra.

As shown in FIG. 1, these experiments identified a 300 base pair fragment from MAGE-1 exon 3 capable of efficient transferring of expression of antigen MZ2E.

EXAMPLE 2

The MAGE-1 gene belongs to a family of several highly related genes. van der Bruggen et al., supra. Prior experiments had noted that MAGE-2 and MAGE-3 did not direct expression of antigen MZ2-E. As the 300 base pair fragment clearly did, the homologous sections of MAGE-2 and MAGE-3 genes were compared to the 300 base pair fragment. Differences were clear, and several 15 amino acid peptides were synthesized, using F-moc for transient N-terminal protection, in accordance with Atherton et al., J. Chem. Soc. 1: 538 (1981). The peptides were purified by C-18 reverse phase HPLC, and characterized by amino acid analysis.

Once the peptides were secured, they were tested in lysis assays, using the chromium release methodology of Boon et al., J. Exp. Med. 152: 1184 (1980). Briefly, 1000 $^{51}$Cr labeled E$^-$ target cells were incubated in 96 well microplates, using various concentrations of peptides for 30 minutes at 37° C.

An equal volume of CTL containing sample was added (cell line 82/30), the number of CTLs being five times that of their target. Chromium release was measured after four hours. Sensitization of E$^-$ cells to lysis by the anti E CTLs was observed with a peptide that corresponds to codons 158–172 of the large open reading frame of MAGE-1. Shorter peptides were prepared and efficient lysis was observed with peptide: Glu Ala Asp Pro Thr Gly His Ser Tyr(SEQ ID NO: 12).

Figure 2:
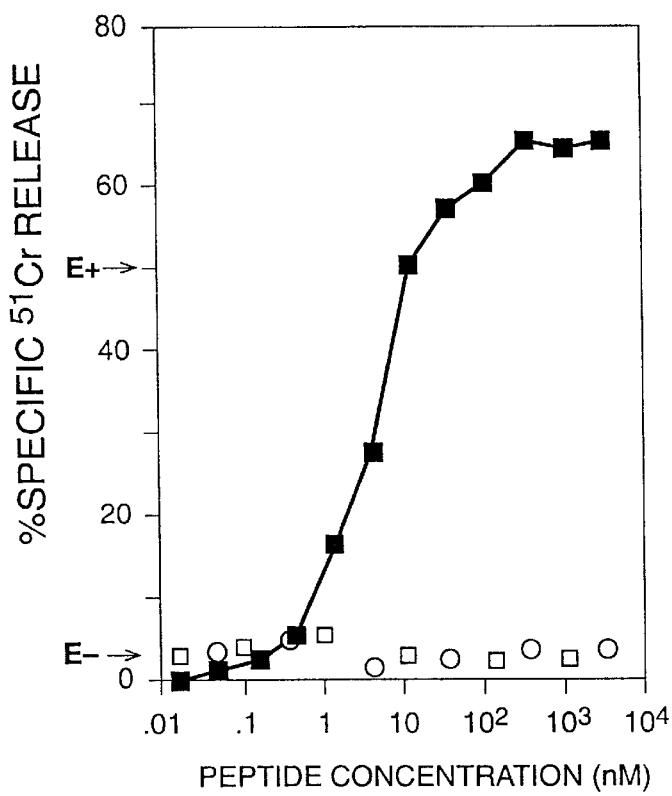
FIG. 2 shows lytic studies in which cells were incubated with various MAGE 1 peptides.

The results, shown in FIG. 2, demonstrate that the first and ninth amino acids were critical for binding and effecting lysis.

This is in accordance with prior reports stating that MHC-I molecules generally are bound by nonapeptides (Rotzschke et al., Nature 348: 252 (1990)). FIG. 2 also shows that half maximum lysis was obtained at a peptide concentration of 5 nM.

EXAMPLE 3

Experiments were carried out to determine what molecule presented the relevant MAGE-1 antigen. To accomplish this, an HLA-A1 gene, as taught by Girdlestone, Nucl. Acids. Res. 18: 6701 (1990), was transfected into a mouse cell line, P1.HTR. This line is a highly transfectable variant of mouse mastocytoma cell line P815. The resulting transfectants, referred to as "P1.HTR.A1", were incubated in the presence of the nonapeptide discussed supra, using the same lysis assay. Controls were also used.

Figure 3A:
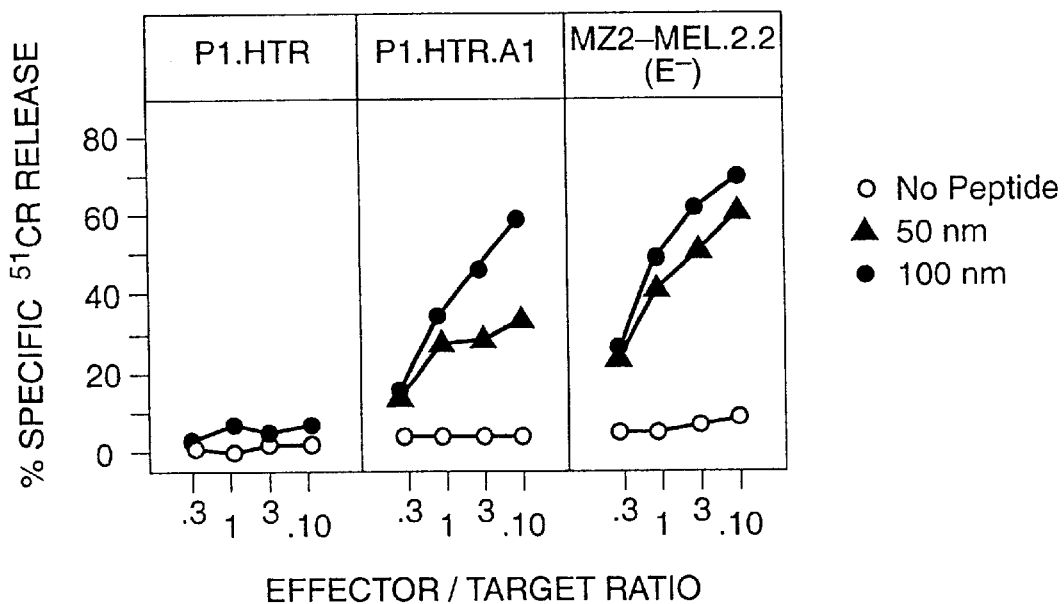
In FIG. 3A, the cell lines P1.HTR, P1.HTR.A1 and MZ2-MEL.2.2 are tested; with no peptide, and at concentrations of 50 nm and 100 nm of peptide.
Figure 3B:
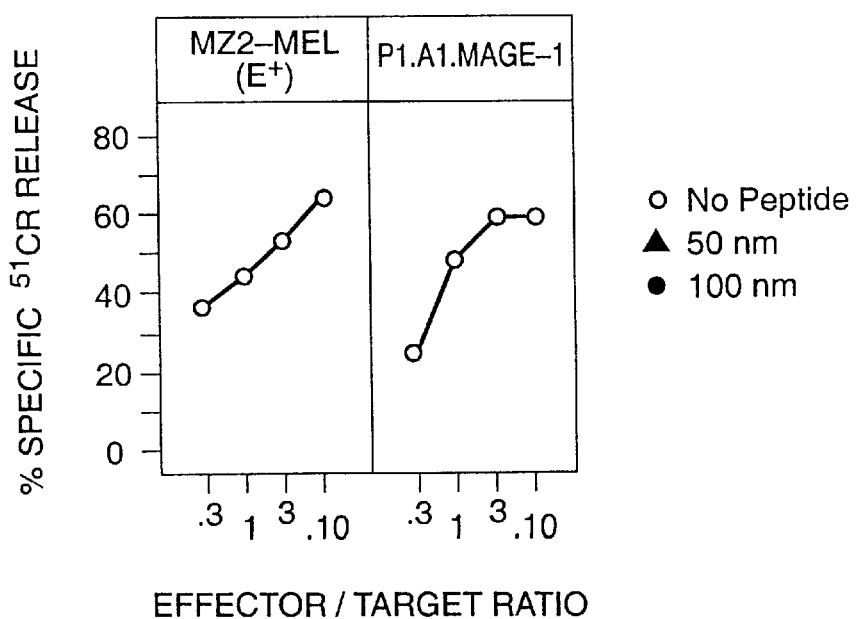
In FIG. 3B, cell lines MZ2-MEL and P1.A1 MAGE-1 were tested with no peptide.

FIG. 3 shows that the cell line was lysed, showing that a model has been developed for screening for a lytic peptide, using a non-human cell.

In experiments not described herein, similar results were obtained with COS cells.

Additional experiments were also carried out, in which cell line P1.HTR A1 was transfected with MAGE-1 cDNA. When the lytic assay of Example 2 was carried out with this co-transfected cells, it was found that they were also lysed.

EXAMPLE 4

Given the homology of the various genes within the MAGE family, a comparison was carried out to identify similarities amongst the homologous regions of the genes. These regions are shown in FIG. 4. These peptides and the nucleic acid sequences coding for them, are not identical, but show a great deal of homology, especially the identical first and ninth residues.

EXAMPLE 5

This example, and examples 6–8 which follow, correspond to examples 37–40 of copending application Ser. No. 08/037,230 filed on Mar. 26, 1993.

A cytolytic CTL clone "20/38" was obtained from peripheral blood lymphocytes of melanoma patient MZ2. This clone is described by Van den Eynde et al., Int. J. Cancer 44: 634–640 (1989), the disclosure of which is incorporated by reference. The CTL clone was isolated following Herin et al., Int. J. Cancer 39: 390–396 (1987), which is incorporated by reference. The assay is described herein, however. Autologous melanoma cells were grown in vitro, and then resuspended at $10^7$ cells/ml in DMEM, supplemented with 10% HEPES and 30% FCS, and incubated for 45 minutes at 37° C. with 200 $\mu$Ci/ml of Na($^{51}$Cr)O$_4$. Labelled cells were washed three times with DMEM, supplemented with 10 mM HEPES. These were then resuspended in DMEM supplemented with 10 mM HEPES and 10% FCS, after which 100 $\mu$l aliquots containing $10^3$ cells, were distributed into 96 well microplates. Samples of the CTL clone were added in 100 ul of the same medium, and assays were carried out in duplicate. Plates were centrifuged for four minutes at 100 g, and incubated for four hours at 37° C. in a 5.5% CO$_2$ atmosphere.

Plates were centrifuged again, and 100 ul aliquots of supernatant were collected and counted. Percentage of $^{51}$Cr release was calculated as follows:

$$\% \ ^{51}Cr \ release = \frac{(ER-SR)}{(MR-SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

These experiments led to isolation of CTL clone 20/38.

Figure 5A:
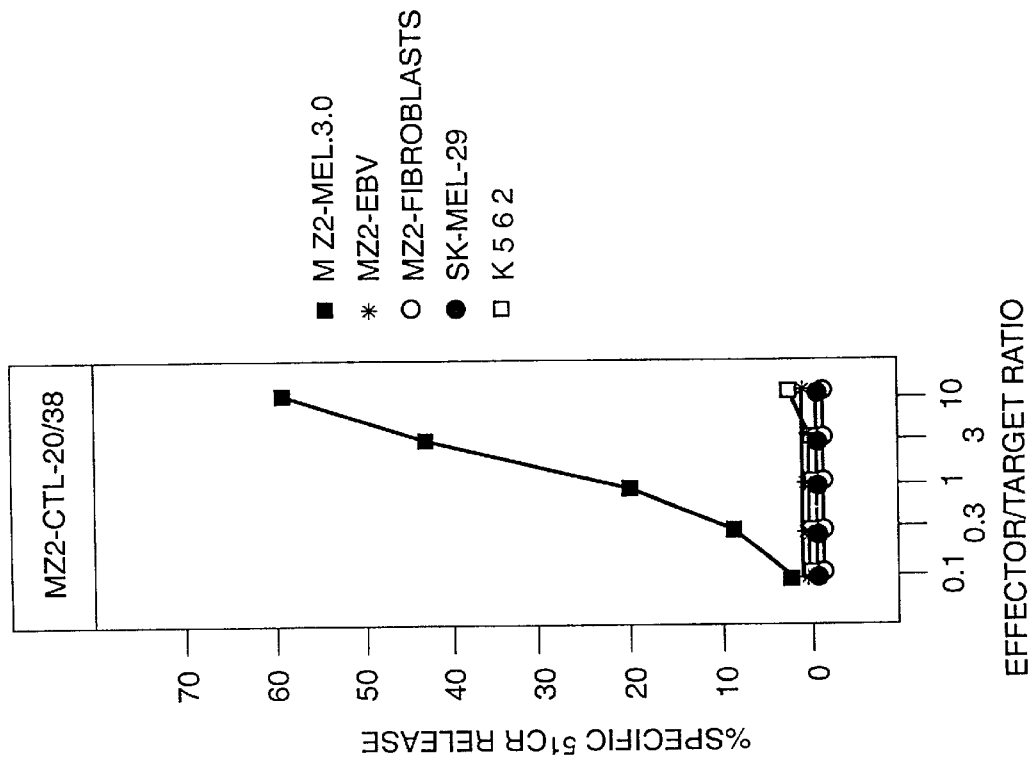
FIG. 5 shows results from a chromium release assay using CTL clone 20/38 on various cell lines.
Figure 5B:
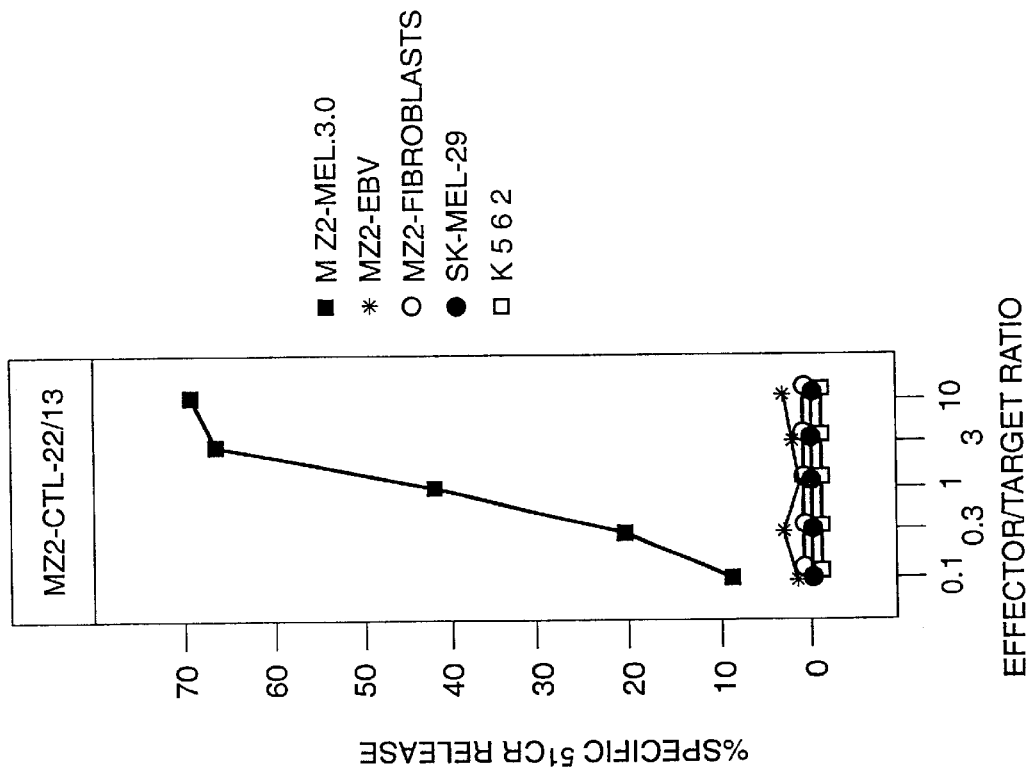
Figure 6A:
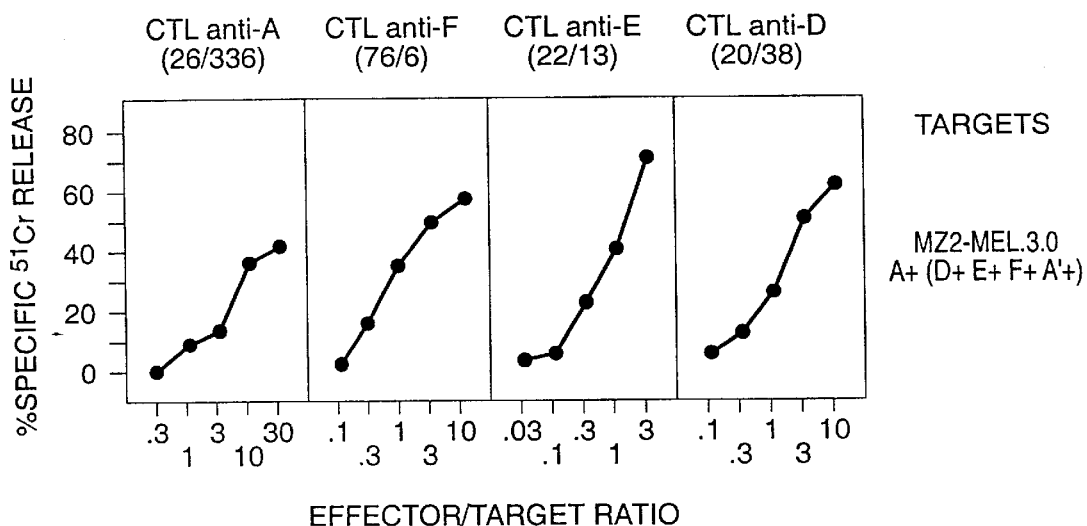
FIG. 6 presents the result of assays undertaken to determine antigenic specificity of CTL clone 20/38.
Figure 6B:
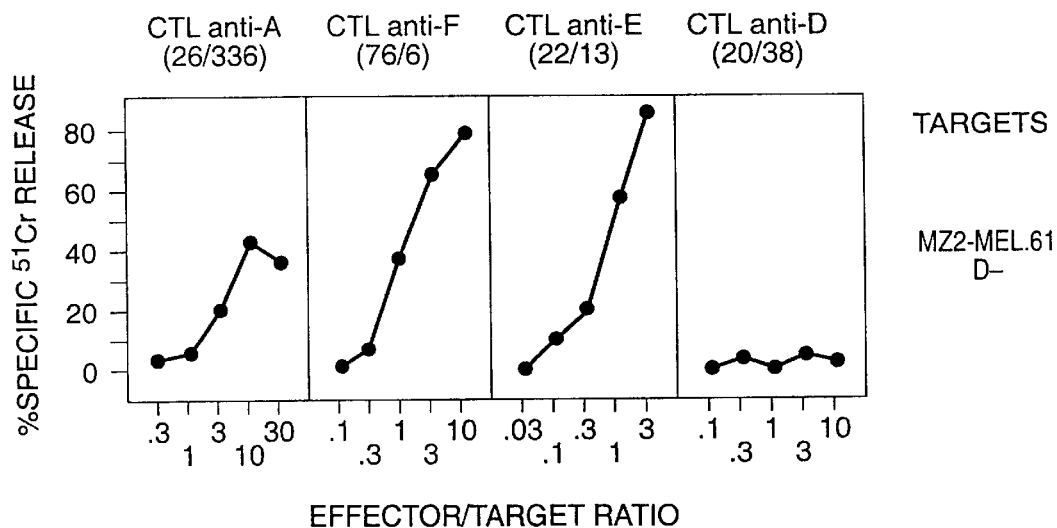
Figure 6C:
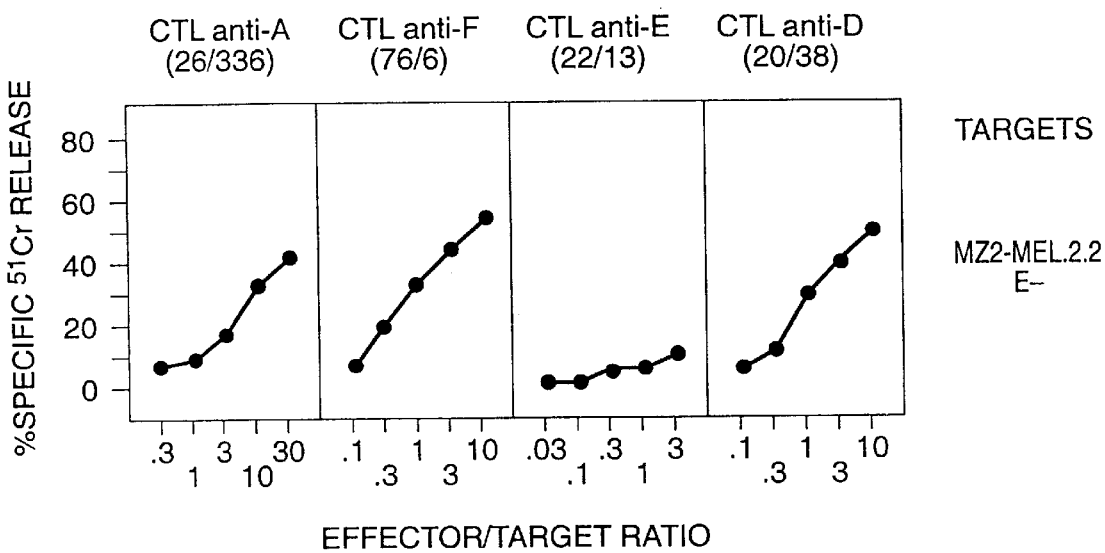
Figure 6D:
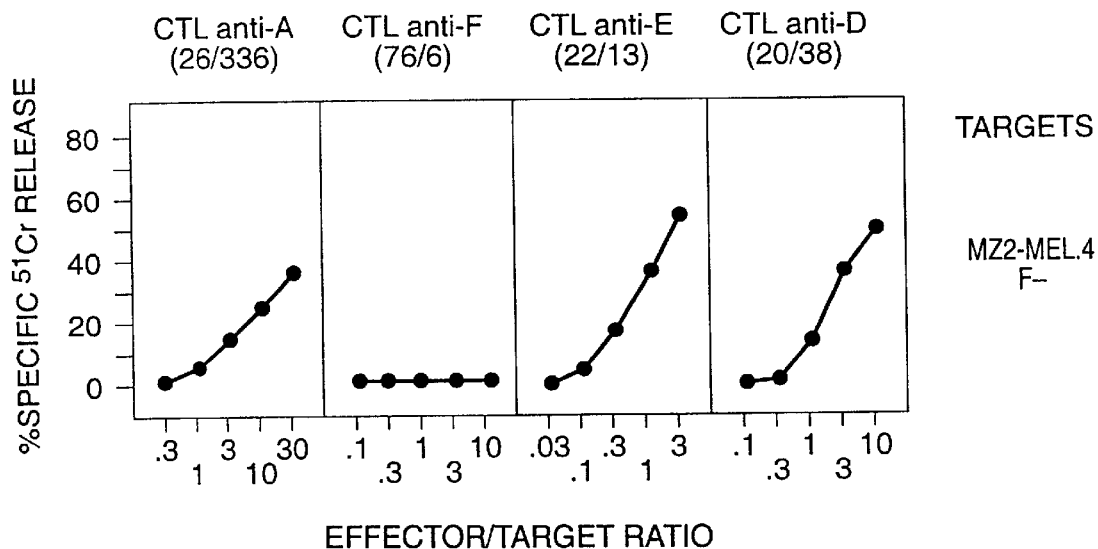

FIG. 5 presents the results of these assays. Specifically, it will be seen that the CTL clone lysed autologous melanoma cell line MZ2-MEL.3.0, but did not lyse EBV-B cell lines, fibroblasts, K562 or non-autologous melanoma cell line SK-MEL-29.

EXAMPLE 6

Once the CTL clone was recognized as being specific for the autologous cell line, it was tested for antigenic specificity. To do this, antigen loss variants derived from patient MZ2 were tested in the same type of chromium release assay described above. These target lines were MZ2-MEL 3.0, which is D+, E+, F+, A+, MZ2-MEL.61, which is D−, MZ2-MEL 2.2, which is E−, and MZ2-MEL.4, which is F−. In addition to CTL clone 20/38, clones which are known to be anti-A (CTL 28/336), anti-F (CTL 76/6), and anti-E (CTL 22/13) were tested.

These results are set forth in FIG. 6. It will be seen that CTL clone 20/38 lysed all the cell lines leading to chromium release except $D^{31}$ cell line MZ2-MEL.61, thus indicating that the CTL clone is anti-D. This result was confirmed, in experiments not included herein, by experiments where TNF release by the CTL clone was observed only in the presence of melanoma lines presenting antigen D.

EXAMPLE 7

Once antigen D was identified as the target molecule, studies were carried out to determine the HLA type which presented it. The experiments described in example A showed that antigen D was presented by MZ2-MEL, and this cell line's HLA specificity is known (i.e., A1, A29, B37, B44, Cw6, C.cl.10). It was also known, however, that a variant of MZ2-MEL which had lost HLA molecules A29, B44 and C.cl.10 still expressed antigen D, so these could be eliminated from consideration. Studies were not carried out on lines expressing B37, as none could be found.

In all, 13 allogeneic lines were tested, which expressed either HLA-A1 (10 of 13), or Cw6 (3 of 13). The cell lines were tested for their ability to stimulate release of TNF by CTL clone 20/38, using the method of Traversari et al., Immunogenetics 35: 145–152 (1992), the disclosure of which is incorporated by reference. This assay measures TNF release via testing toxicity of supernatants on WEHI 164–13 cells.

In the assays, cell samples (3000, 10,000 or 30,000 cells) from the allogeneic lines were cultured in the presence of 1500 cells of the CTL clone, and 25 u/ml of IL-2. Twenty-four hours later, the supernatant from the culture was tested against the WEHI cells for toxicity. The results are presented in Table 1, which follows.

Eight cell lines were found to stimulate TNF release from the CTL clone 20/38, All of these lines were HLA-A1, None of the Cw6 presenting lines did so. The cell lines were also assayed to determine MAGE expression. All eight of the lines which stimulated TNF release expressed MAGE-3, whereas the two HLA-A1 lines which were negative did not.

TABLE 1

| Melanoma | Number of cells | TNF pg/ml | | | | Expression of Mage-3 | Expression of HLA-A1 |
|---|---|---|---|---|---|---|---|
| | | Exp 1 | | Exp 2 | | | |
| | | * | +CTL 20/38 | * | +CTL 20/38 | | |
| MZ2-MEL-61.2 | 50000 | | 1 | | 4 | +++ | + |
| MZ2-MEL-ET1 | 50000 | | >120 | | >120 | +++ | + |
| | 1666 | | 66 | | >120 | | |
| LY-1-MEL | 30000 | 1 | >120 | 1 | >120 | +++ | + |
| | 10000 | 1 | >120 | 1 | >120 | | |
| | 3000 | <1 | 114 | 2 | >120 | | |
| MI-10221 | 30000 | <1 | >120 | | | +++ | + |
| | 10000 | <1 | 71 | | | | |
| | 3000 | <1 | 74 | | | | |
| LY-2-MEL | 30000 | 1 | 57 | | | +++ | + |
| | 10000 | 1 | 86 | | | | |
| | 3000 | 1 | 91 | | | | |
| LY-4-MEL | 30000 | 1 | >120 | | | +++ | + |
| | 10000 | 1 | >120 | | | | |
| | 3000 | 1 | >120 | | | | |
| SK23-MEL | 30000 | 1 | 112 | | | ++++ | + |
| | 1000 | 1 | 116 | | | | |
| | 3000 | 1 | 105 | | | | |
| MI-665/2-MEL | 30000 | 1 | 3 | 2 | 4 | − | + |
| | 10000 | 1 | 2 | 2 | 5 | | |
| | 3000 | 1 | 5.2 | 1 | 5 | | |
| LB34-MEL | 30000 | 1 | >120 | | | ++++ | + |
| | 10000 | 1 | >120 | | | | |

TABLE 1-continued

| Melanoma | Number of cells | Exp 1 | | Exp 2 | | Expression of Mage-3 | Expression of HLA-A1 |
|---|---|---|---|---|---|---|---|
| | | * | +CTL 20/38 | * | +CTL 20/38 | | |
| | 3000 | 1 | >120 | | | | |
| LB45-MEL | 30000 | 1 | 11 | 1 | 30 | – | + |
| | 10000 | 1 | 6 | 1 | 12 | | |
| | 3000 | 1 | 2 | <1 | 7 | | |
| NA-6-MEL | 30000 | 1 | 77 | 5 | 98 | +++ | + |
| | 10000 | 1 | 164 | 5 | >120 | | |
| | 3000 | 1 | 110 | 4 | >120 | | |
| MI-13443-MEL | 30000 | 1 | >120 | | | ++++ | + |
| | 10000 | 1 | >120 | | | | |
| | 3000 | 1 | >120 | | | | |
| LB5-MEL | 30000 | 1 | 8 | 4 | 9 | + | – |
| | 10000 | <1 | 5 | 4 | 11 | | |
| | 3000 | <1 | 5 | 1 | 5 | | |
| SK64-MEL | 30000 | 1 | 4 | 2 | 5 | ? | – |
| | 10000 | 1 | 2 | 1 | 5 | | |
| | 3000 | 1 | 1 | 1 | 4 | | |
| LB33-MEL | 30000 | | | 1 | 3.5 | +++ | – |
| | 10000 | | | 1 | 4 | | |
| | 3000 | | | 1 | 3 | | |
| LB73-MEL | 30000 | | 16 | | | – | – |

1500 CTL 20/38 and 25 n/ml IL2 were mixed with the indicated number of cells of the different allogeneic melanomas. 24 hours later, the amount of TNF present in the supernatant was assayed by testing its cytotoxicity for WEHI-164-13 cells.

EXAMPLE 8

In view of the results set forth in example 7, experiments were carried out to determine if antigen D was in fact a tumor rejection antigen derived from MAGE-3. To do this, recipient COS-7 cells were transfected with 100ng of the gene for HLA-A1 cloned into pcDNA I/Amp, and 100 ng of one of (a) cDNA for MAGE-1 cloned into pcDNA I/Amp, (b) cDNA for MAGE-2 cloned into pcDSRα, or (c) cDNA for MAGE-3 cloned into pcDSRα. The transfecting sequences were ligated into the plasmids in accordance with manufacturer's instructions. Samples of COS-7 cells were seeded, at 15,000 cells/well into tissue culture flat bottom microwells, in Dulbeco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, and the plasmids described above. Following four hours of incubation at 37° C., the medium was removed, and replaced by 50 μl of PBS containing 10% DMSO. This medium was removed after two minutes and replaced by 200 μl of DMEM supplemented with 10% of FCS.

Figure 7:
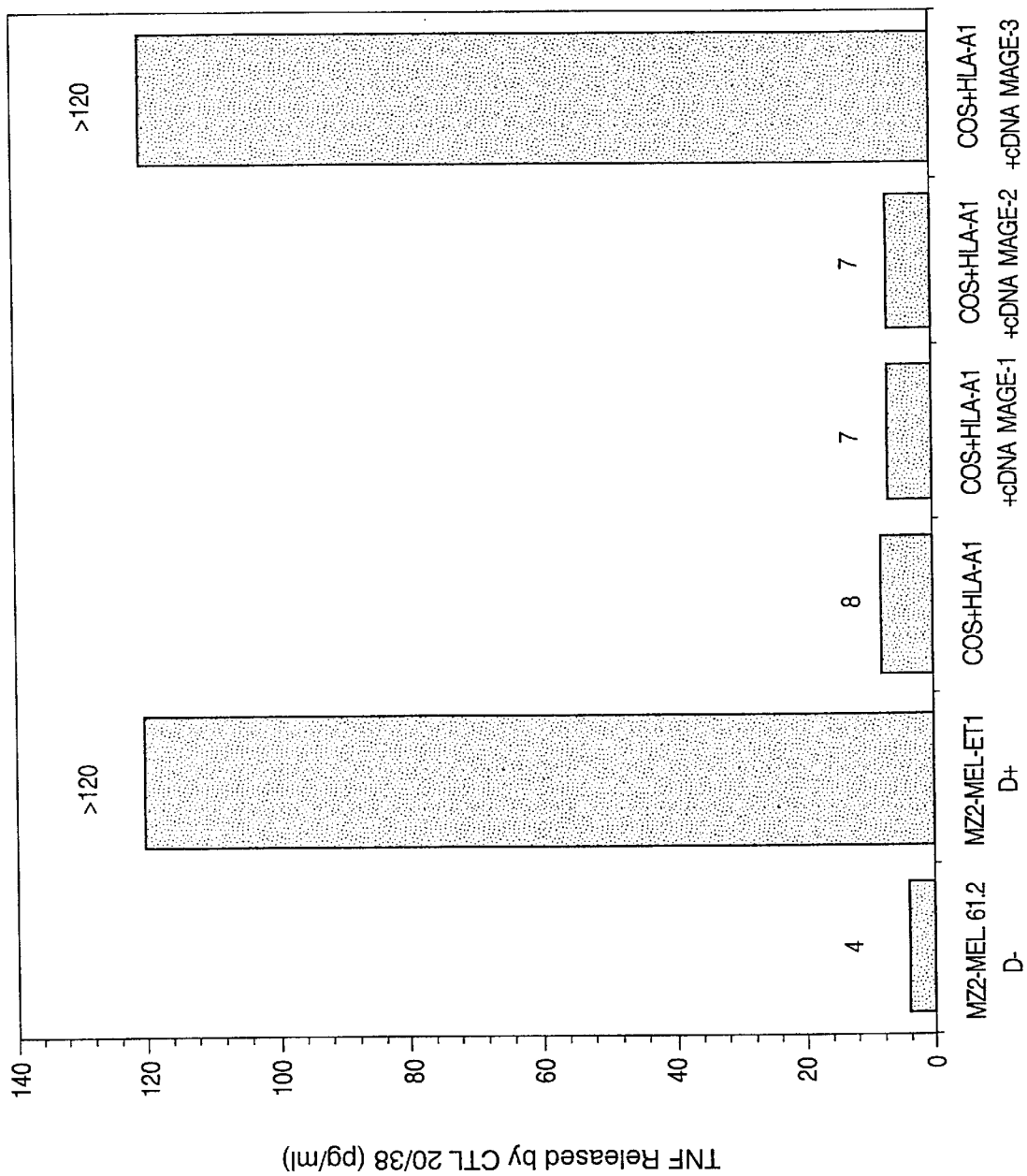
FIG. 7 shows the results obtained when a TNF release assay was carried out on various transfected cells.

Following this change in medium, COS cells were incubated for 24 hours at 37° C. Medium was then discarded, and 1500 cells of CTL clones 20/38 were added, in 100 μl of Iscove medium containing 10% pooled human serum, supplemented with 25 u/ml of IL-2. Supernatant was removed after 24 hours, and TNF content was determined in an assay on WEHI cells, as described by Traversari et al., Immunogenetics 35: 145–152 (1992), the disclosure of which is incorporated by reference. These results are shown in FIG. 7.

It will be seen that the CTL clone was strongly stimulated by COS7 cells transfected with HLA-A1 and MAGE-3, but not by the cells transfected with the other image genes. This leads to the conclusion that antigen D is a tumor rejection antigen derived from the tumor rejection antigen precursor coded by gene MAGE-3, and that this TRA is presented by HLA-A1 molecules.

EXAMPLE 9

Further experiments were carried out using peptide Glu Val Asp Pro Ile Gly His Leu Tyr (SEQ ID NO: 17) which is derived from the gene "MAGE".

The peptide was prepared in the same manner as were the peptides of example 2. The chromium release assay described in that example was also used. Cell line MZ2-MEL 61.2, which is an antigen D loss variant of MZ2.MEL43 was labelled with $^{51}Cr$, and was then tested with antigen D specific cytolytic cell clone CTL 20/38, and varying concentrations of the peptide. MZ2-MEL61.2 and CTL 20/38 were combined in a 1.5:1 ratio, together with the peptide at varying concentrations. The mixture was incubated for four hours, after which chromium release was measured. As a control, chromium labelled MZ2-MEL.43 was used.

Figure 8:
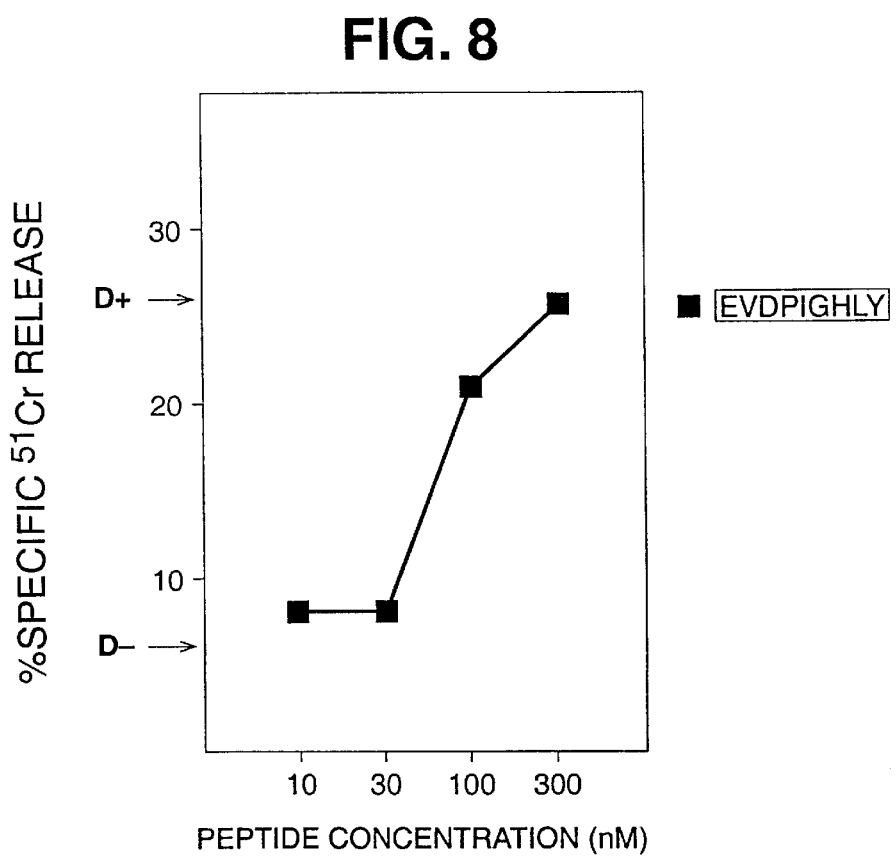
FIG. 8 sets forth the results of a lytic assay using the peptide of the invention using the peptide set forth in SEQ ID NO: 17.

The results, presented in FIG. 8, show that the peptide does act as a tumor rejection antigen in that the cytolytic T cell clones recognize and lyse the targeted cells.

The foregoing examples show that a nonapeptide derived from MAGE-3 is presented by HLA-A1 molecules, and cells presenting the complex of HLA-A1 and the nonapeptide are recognized and lysed by specific CTL cells. This observation indicates that the nonapeptide of the invention may be used both therapeutically and diagnostically.

In the case of the latter category of use, the nonapeptide may be used, for example, to identify tumors expressing a particular HLA molecule, or cancer cells per se. One contacts a cancer cell containing sample or a tumor cell with the nonapeptide which binds thereto, and combines the material with a CTL sample specific for the complex. If lysis ensues, then the tumor/cancer cell can be identified as HLA-A1 presenters.

Therapeutically, there are two major ways in which the nonapeptide may be used. In an in vivo therapeutic approach, the nonapeptide may be administered in a way which targets it to tumors to be treated. This can be done via direct injection, time release administration, coupling to tumor specific antibodies, and so forth. Upon binding to HLA-A1 molecules, there is a CTL response, leading to lysis of the tumor. Of course, in such a therapeutic approach, the nonapeptide is administered in an amount sufficient to lead to lysis of the tumor. This amount will vary, based upon the particular patient, the type and size of the tumor, and so forth.

An "in vitro" form of therapy is also contemplated. As indicated supra, when HLA-A1 molecules bind to the MAGE-3 derived nonapeptide, if contacted with the CTLs specific for the peptide/HLA complex, a CTL proliferative response occurs. As the CTLs are the agents of tumor lysis in vivo, the resulting expanded populations may be administered to the patient. The CTLs can be expanded by using the patient's own blood or any other source of CTLS, or by contact to samples of peptide specific CTLs which have previously been established. In this regard, note that CTL 20/38, discussed supra had been available for some time as was the methodology for its development.

Therapies of the type described herein are particularly useful for melanoma. Analysis of samples has shown that about 26% of the Caucasian population at large presents HLA-A1 allele. Thus, at the least, 26% of the Caucasian melanoma population may be considered as potential subjects for therapy with the peptide. The patents may also be treated with proliferative cells which have complexes of HLA-A1 and the nonapeptide presented on their surface.

The nucleic acid sequences, as indicated, may be used in a variety of ways. MAGE genes are expressed in tumors, and thus the nucleic acid sequences may be used a probes to identify tumor cells. This can be accomplished via labelled hybridization probes, PCR, or any of the various nucleic acid probe based assays known to the art.

The development of the non-human cell lines described herein presents a unique way to carry out some of the features of the invention described herein. The examples show, e.g., that the CTLs recognize the complex of HLA and nonapeptide, and do not appear to differentiate between the cell types which present the complexes. Thus, the isolated, non-human cell lines of the invention can be used to generate CTLS, and to identify their presence in human samples.

As indicated, the invention also involves isolated non-human cell lines transfected with both an HLA-A1 gene, and a sequence coding for the nonapeptide. One is not limited to transfection with one HLA coding gene and one MAGE peptide, and indeed the invention contemplates polytransfected cells, which may contain more than one HLA gene and more than one MAGE antigen coding sequence. Given the finding that both a MAGE-1 derived nonapeptide and a MAGE-3 derived nonapeptide are presented by a common HLA molecule supports this contention. Such cells may be regarded as universal effector cells, as the presence of appropriate pairs of HLA and peptide on the surface will lead either to identification of specific CTLs of choice, or to generation of CTL proliferation in a therapeutic context. Such cells, be they cotransfected or polytransfected, may serve as vaccines when combined with a suitable adjuvant, such as those well known to the art. Treatment of various cancerous conditions, such as melanoma and breast cancer, may be carried out using these transfectant.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for identifying tumor or cancer cells which express a particular HLA molecule, comprising contacting tumor or cancer cells with a nonapeptide, the amino acid sequence of which is set forth at SEQ ID NO: 17 wherein said nonapeptide binds to said HLA molecule to form a complex, contacting said tumor or cancer cells with a cytolytic T cells specific for said complex and determining lysis of tumor or cancer cells presenting the complex on their surfaces, so as to identify said tumor or cancer cells.

2. The method of claim 1, wherein said HLA molecule is HLA-A1.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: genomic DNA (ix) FEATURE:
      (A) NAME/KEY: MAGE-1 nonapeptide coding sequence (xi) SEQUENCE DESCRIPTION: SEQ ID NO: 1:

GAAGCAGACC CCACCGGCCA CTCCTAT                                                      27

(2) INFORMATION FOR SEQ ID NO: 2:

(i) SEQUENCE CHARACTERISTICS:
      (A) LENGTH: 27 base pairs
      (B) TYPE: nucleic acid
      (C) STRANDEDNESS: single

```
        (D) TOPOLOGY: linear (ii) MOLECULE TYPE: genomic DNA (ix) FEATURE:
        (A) NAME/KEY:  MAGE-2 nonapeptide coding sequence (xi) SEQUENCE DESCRIPTION: SEQ ID NO: 2:

GAAGTGGTCC CCATCAGCCA CTTGTAC                                          27

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY:  MAGE-21 nonapeptide coding sequence (xi) SEQUENCE DESCRIPTION: SEQ ID NO: 3:

GAAGTGGTCC GCATCGGCCA CTTGTAC                                          27

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY:  MAGE-3 nonapeptide coding sequence (xi) SEQUENCE DESCRIPTION: SEQ ID NO: 4:

GAAGTGGACC CCATCGGCCA CTTGTAC                                          27

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY:  MAGE-4 nonapeptide coding sequence (xi) SEQUENCE DESCRIPTION: SEQ ID NO: 5:

GAAGTGGACC CCGCCAGCAA CACCTAC                                          27

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY:  MAGE-41 nonapeptide coding sequence
```

(xi) SEQUENCE DESCRIPTION: SEQ ID NO: 6:

GAAGTGGACC CCACCAGCAA CACCTAC                                   27

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY:  MAGE-5 nonapeptide coding sequence (xi) SEQUENCE DESCRIPTION: SEQ ID NO: 7:

GAAGCGGACC CCACCAGCAA CAACTAC                                   27

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY:  MAGE-51 nonapeptide coding sequence (xi) SEQUENCE DESCRIPTION: SEQ ID NO: 8:

GAAGCGGACC CCACCAGCAA CACCTAC                                   27

(2) INFORMATION FOR SEQ ID NO: 9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY:  MAGE-6 nonapeptide coding sequence (xi) SEQUENCE DESCRIPTION: SEQ ID NO: 9:

GAAGTGGACC CCATCGGCCA CGTGTAC                                   27

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

CAGGGAGCCA GTCACAAAG                                            19

(2) INFORMATION FOR SEQ ID NO: 11:

(i) SEQUENCE CHARACTERISTICS:
        (A) LENGTH: 20 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO: 11:

ACTCAGCTCC TCCCAGATTT                               20

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

Glu Ala Asp Pro Thr Gly His Ser Tyr
                5

(2) INFORMATION FOR SEQ ID NO: 13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

Glu Ala Asp Pro Thr Gly His Ser
                5

(2) INFORMATION FOR SEQ ID NO: 14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

Ala Asp Pro Thr Gly His Ser Tyr
                5

(2) INFORMATION FOR SEQ ID NO: 15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

Glu Val Val Pro Ile Ser His Leu Tyr
                5

(2) INFORMATION FOR SEQ ID NO: 16:

(i) SEQUENCE CHARACTERISTICS:
        (A) LENGTH: 9 amino acids
        (B) TYPE: amino acid

```
            (C) STRANDEDNESS: single
            (D) TOPOLOGY: linear (ii) MOLECULE TYPE: protein (xi) SEQUENCE DESCRIPTION: SEQ ID NO: 16:

Glu Val Val Arg Ile Gly His Leu Tyr
                5

(2) INFORMATION FOR SEQ ID NO: 17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 17:

Glu Val Asp Pro Ile Gly His Leu Tyr
                5

(2) INFORMATION FOR SEQ ID NO: 18:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 18:

Gly Val Asp Pro Ala Ser Asn Thr Tyr
                5

(2) INFORMATION FOR SEQ ID NO: 19:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 19:

Glu Val Asp Pro Thr Ser Asn Thr Tyr
                5

(2) INFORMATION FOR SEQ ID NO: 20:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 20:

Glu Ala Asp Pro Thr Ser Asn Thr Tyr
                5

(2) INFORMATION FOR SEQ ID NO: 21:

(i) SEQUENCE CHARACTERISTICS:
            (A) LENGTH: 9 amino acids
```

```
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 21:

Glu Ala Asp Pro Thr Ser Asn Thr Tyr
              5

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 22:

Glu Val Asp Pro Ile Gly His Val Tyr
```